(12) United States Patent
Ortega Quijano et al.

(10) Patent No.: US 12,283,371 B2
(45) Date of Patent: Apr. 22, 2025

(54) SYSTEM FOR MONITORING A CLINICAL SCENARIO

(71) Applicant: Deneb Medical, S.L., San Sebastián (ES)

(72) Inventors: Noé Ortega Quijano, San Sebastián (ES); Oliver Rubio Zamora, Irún (ES); Álvaro García Martínez, Valencia (ES); Javier Laguardia Arraiza, Pamplona (ES)

(73) Assignee: Deneb Medical, S.L. (ES)

( * ) Notice: Subject to any disclaimer, the term of this patent is extended or adjusted under 35 U.S.C. 154(b) by 501 days.

(21) Appl. No.: 17/782,874

(22) PCT Filed: Dec. 4, 2019

(86) PCT No.: PCT/ES2019/070825
§ 371 (c)(1),
(2) Date: Jun. 6, 2022

(87) PCT Pub. No.: WO2021/111015
PCT Pub. Date: Jun. 10, 2021

(65) Prior Publication Data
US 2023/0030273 A1 Feb. 2, 2023

(51) Int. Cl.
*G16H 40/40* (2018.01)
*G06T 7/246* (2017.01)
*G06T 7/30* (2017.01)
*G06V 10/22* (2022.01)
*G06V 10/24* (2022.01)
*G06V 20/52* (2022.01)

(52) U.S. Cl.
CPC ............. *G16H 40/40* (2018.01); *G06T 7/246* (2017.01); *G06T 7/30* (2017.01); *G06V 10/22* (2022.01); *G06V 10/245* (2022.01); *G06V 20/52* (2022.01)

(58) Field of Classification Search
None
See application file for complete search history.

(56) References Cited

U.S. PATENT DOCUMENTS

2014/0270436 A1 9/2014 Dascal et al.
2015/0018682 A1 1/2015 Schers et al.
2018/0325415 A1* 11/2018 Ehrl .................. G06T 7/246

OTHER PUBLICATIONS

International Search Report for PCT/ES2019/070825 dated Aug. 6, 2020. 3 pgs.

* cited by examiner

*Primary Examiner* — Vincent Rudolph
*Assistant Examiner* — Basel Aziz Musaed
(74) *Attorney, Agent, or Firm* — Lerner David LLP

(57) ABSTRACT

The present invention relates to a system for monitoring a non-static clinical scenario, preferably a surgical field, such that different elements of interest can be located throughout the entire clinical event; in particular, a high-precision monitoring and distinction of critical biological tissues, such as nerves or blood vessels, is sought.

25 Claims, 3 Drawing Sheets

SYSTEM FOR MONITORING A CLINICAL SCENARIO

CROSS-REFERENCE TO RELATED APPLICATIONS

The present application is a national phase entry under 35 U.S.C. § 371 of International Application No. PCT/ES2019/070825, filed Dec. 4, 2019, the disclosure of which is incorporated herein by reference.

OBJECT OF THE INVENTION

The present invention relates to a system for monitoring a non-static clinical scenario, preferably a surgical field, such that different elements of interest can be located throughout the entire clinical event; in particular, a high-precision monitoring and distinction of critical biological tissues, such as nerves or blood vessels, is sought.

BACKGROUND OF THE INVENTION

The detection and imaging techniques for the distinction of biological tissues are of enormous interest in the clinical field, since they allow revealing the presence of critical structures, such as nerves, blood vessels, glands, or tumors present in said biological tissue. As a result, the possibilities of its application for diagnosis, surgery, treatment are substantial.

Under laboratory conditions, these techniques are validated on fixed samples. However, when applying said techniques to clinical scenarios an important obstacle imposed by the actual conditions of the clinical scenario itself arises, and it is that said scenario is not static. The mobility of the scenario is due to a number of factors, including the patient's breathing, movements produced by contact and pressure of the medical personnel and instruments on tissues, vibrations, and other isolated events that cannot be ruled out, such as, for example, spasms, accidental shocks, etc.

This problem is worse in certain advanced imaging techniques which allow displaying and distinguishing tissues with high precision across a large area or even a large volume. In these cases, prolonged data measurement and/or post-processing times are normally required, in which case it increases the probability that movements of the clinical scenario are produced.

The information relating to the distinction of a tissue has to be updated throughout the entire clinical event, i.e., once an initial distinction measurement is available, said measurement will have to vary according to the movements of the clinical scenario over time. With this information update, it is possible to know, for example, if a nerve distinguished by the system that was in an initial position has been displaced to another different position after the movement of the clinical scenario.

This information is highly relevant, on one hand, for the positioning of the actual tissue distinction system, and on the other hand, because it serves as support information for the clinical personnel or the robotic system in charge of the intervention, if it were required.

In this context, object monitoring algorithms, which are well known in the area of machine vision or computer vision, are crucial. Said algorithms allow, by analyzing a set of images, recognizing and monitoring objects in said images by measuring variations in the position of the object (in general, translations and rotations) between consecutive images.

The current application of monitoring algorithms to clinical scenarios is typically based on RGB images acquired by means of one or more cameras. From the entire image, the monitoring algorithm performs, firstly, a selection of characteristic points of the image. The chosen characteristic points play the role of reference points which must be completely or partially located in the following images for the purpose of inferring movement of the object with respect to the measurement system and thus performing monitoring of the clinical scenario.

Current monitoring algorithms have two limitations:
- The selection of characteristic points is performed based on purely visual criteria, such as for example luminosity, contrast, roughness, etc.
- The monitoring of characteristic points preferably assumes that the object is a rigid solid, and that, therefore, the entire network of points is subjected to the same rotations and translations.

In the first case, the characteristic points are chosen without knowing anything about the type of tissues present in the images, i.e., monitoring of any of the elements displayed in the images is performed without taking into account which structures are of greater interest. However, in a clinical event, it is most common for the critical structures to constitute a small sub-region within the entire image and it is in said structures where maximizing precision of the monitoring is of most interest.

In the second case, the drawback is that the monitoring methods are valid for hard, non-deformable tissues and/or structures, such as bone, but they make mistakes in the monitoring of soft tissues. Although there are monitoring methods specifically designed for deformable tissues, they require considerably increasing the number of characteristic points of the image to enable modeling, in the most precise manner possible, the manner in which deformation of the tissue is produced, which entails unacceptable computation times in clinical applications in realistic conditions.

The following invention proposes a solution to the aforementioned problems by means of a system for monitoring a non-static clinical scenario which is capable of achieving high precision in the monitoring of structures of special interest throughout the entire clinical event.

DESCRIPTION OF THE INVENTION

The present invention proposes a solution to the aforementioned problems by means of a system for monitoring a clinical scenario according to claim 1. Preferred embodiments of the invention are defined in the dependent claims.

A first inventive aspect provides a system for monitoring a clinical scenario comprising:
a) a control module with processing capacity;
b) a viewing unit, connected to the control module and controlled by said control module, adapted for capturing images of a clinical scenario within its field of vision, wherein the captured images provide information about the orientation, shape, and position of said clinical scenario; and wherein the control module and the viewing unit are configured for:
  capturing, by means of the viewing unit, at least one initial monitoring image of the clinical scenario within the field of vision of the viewing unit;
  capturing, by means of the viewing unit, a plurality of monitoring images of the clinical scenario within the field of vision of the viewing unit in different instants in time, where i is an index indicating the time instant of capture of the captured i-th monitoring image;

by means of a monitoring algorithm executed in the control module:

determining a plurality of initial characteristic reference points belonging to the clinical scenario and shown in the at least one initial monitoring image, and establishing their spatial position;

for each of the monitoring images, determining a plurality of characteristic reference points belonging to the clinical scenario, which match characteristic reference points determined in the immediately preceding monitoring image, and establishing their spatial position;

determining a transformation relating the position of the characteristic reference points determined in instant i with the position of the corresponding characteristic reference points determined in instant i−1;

and wherein the system is characterized in that the control module is additionally configured for receiving or generating at least one region of interest when the captured monitoring image is the at least one initial monitoring image and spatially positioning the at least one region of interest with respect to each monitoring image, and in that the monitoring algorithm is configured such that the concentration of characteristic reference points in the at least one region of interest is greater than the concentration of characteristic reference points in the rest of the monitoring image.

Throughout this document, clinical scenario will be understood to be the set of elements or structures on which a clinical event such as a surgery, a diagnosis, or a treatment, is carried out. Preferably, the clinical event is a surgery and the clinical scenario is a surgical field comprising biological tissues and possibly another type of elements present during said surgery; for example, surgical instruments, gauze and swabs, a robotic system in charge of the operation or the hands of the actual medical personnel. Medical, clinical, or health personnel are to be understood to be any professional who works in medicine and can intervene in the surgical, diagnostic, or treatment procedure, for example, surgeons, nurses, or assistants.

A clinical scenario, in general, is not static but rather changes over time due to a number of factors, inter alia, the patient's breathing, the movements produced by contact and pressure of the medical personnel and instruments on tissues, vibrations, or spasms of the patient.

The system of the invention allows performing monitoring of the elements of a clinical scenario with high precision. To that end, it has two elements: a control module and a viewing unit. Control module is to be understood to be a set of computational means with data processing capacity; for example, a computer or a microcontroller. Viewing unit is to be understood to be at least one visual component adapted for capturing images; for example, one or more RGB cameras or a radiological imaging system.

The control module and the viewing unit are connected to one another and work together for carrying out the monitoring of the clinical scenario. Preferably, the control module sends instructions to the viewing unit and receives data from same for processing thereof.

The viewing unit comprises a specific field of vision or field of view, understanding as such the area of the clinical scenario which the viewing unit can capture. Thus, the viewing unit captures or acquires images within that part of the clinical scenario which is visible or can be captured through its field of vision.

Firstly, the viewing unit captures at least one initial monitoring image of the clinical scenario so as to obtain information about the orientation, shape, and position of the tissues and other elements comprised in said clinical scenario. This at least one image will serve as a starting point to perform monitoring of the clinical scenario—of said tissues and other elements—over time by means of the analysis of new monitoring images captured by the viewing unit in different i-th instants in time. Throughout the document, the index i indicates the time instant in which the viewing unit captures a different monitoring image, without prejudice to the fact that this notation may be modified.

The control module receives the images captured by the viewing unit for processing them and carrying out the monitoring of the clinical scenario. Said processing is based on a monitoring algorithm. Throughout this document, monitoring algorithm will be understood to be the set of mathematical, geometric, or logical instructions or rules, executed by the control module, capable of recognizing visible objects in the monitoring images and establishing a match between them. The monitoring algorithm can thereby estimate the positions of one and the same object in two different monitoring images and calculating the necessary transformation that would have to be applied on an image captured in a given instant in time so as to obtain the object positioned as it is presented in the other image captured in another instant in time.

In the context of the invention, object recognition based on the determination of a plurality of characteristic reference points in the monitoring images captured by the viewing unit. Throughout the document, characteristic reference points—or simply reference points—are to be understood to be pixels or pixel regions readily distinguishable with respect to their environment, for example:

1) characteristic points or regions of the image, such as a mole in the skin or luster in a surgical instrument; or
2) specific colors of the image, such as the red color of blood or the metallic luster of surgical instruments; or
3) specific textures of the image, such as the aqueous texture of given fluids; or
4) regions of the image with high contrast with respect to their environment, such as the presence of a tumor; or
5) regions of the image with a high heterogeneity with respect to their environment, such as the presence of a set of blood vessels opposite a homogeneous area such as the skin; or
6) a combination of any of the foregoing.

The characteristic reference points serving as a starting point to perform monitoring of the clinical scenario are determined by means of the monitoring algorithm in the at least one initial monitoring image. Once said points have been determined, their spatial position is established, and this will serve as a reference for the monitoring itself.

It is understood that the computational system of the control module or of the viewing unit makes use of a spatial coordinate system where it establishes a match between the points observed in the images captured by the viewing unit and points in said space.

In following i-th instants in time, the monitoring algorithm determines the characteristic reference points in each of the i-th monitoring images. These new reference points, a priori, match the reference points captured in the previous instant in time—where said previous instant in time may be the initial instant in time. Once the new reference points have been determined, the monitoring algorithm establishes their spatial position according to the pre-established coordinate system.

Finally, the monitoring algorithm determines which transformation relates with higher precision—or less error—the positions of the new reference points of a monitoring image with the reference points of the immediately preceding monitoring image. Said transformation is preferably an affine transformation which will comprise at least one rotation and one displacement.

If additional information type does not exist, the monitoring algorithm determines the characteristic reference points distributed over the entire monitoring image such that there is a compromise between the monitoring of all the elements appearing in the monitoring image—tissues and other elements of the clinical scenario—and the precision attained in said monitoring. The monitoring algorithms capable of carrying out these functions are known.

However, the control module is additionally configured for receiving or for generating additional information which improves the precision in the monitoring of those parts of the clinical scenario that are of greater interest. Throughout the document, receiving information will be understood to be that said information comes from an element other than the control module itself, whereas generating information will be understood to mean it is the control module itself that produces said additional information.

The additional information comprises one or more regions of interest. Throughout the document, a region of interest will be understood to be a sub-region of a monitoring image in which there appear elements of the clinical scenario with respect to which a higher precision monitoring is to be obtained. This region or these regions of interest are spatially positioned with respect to the monitoring images by means of the control module.

In a particular example, the control module neither receives nor generates a region of interest, so a default region of interest corresponding to a subset of the entire viewing unit is used.

The region of interest establishes a sub-domain of dimensions that are strictly smaller than the field of vision of the viewing unit.

Preferably, the region or regions of interest comprise critical structures. Throughout this document, structure will be understood to be any of the elements present in the clinical scenario and critical structure will be understood to be that structure on which high precision monitoring is required to be performed. For example, if the clinical event is a surgery, a very comprehensive monitoring of critical structures such as the nerves or blood vessels should be performed in order to know their spatial position in quasi real time, and thereby prevent medical personnel or a robotic system in charge of the operation from intervening or even sectioning said critical structures.

This comprehensive monitoring is achieved as a result of the monitoring algorithm being additionally configured to focus the determination of characteristic reference points in the region or regions of interest, such that every time the algorithm determines reference points in a monitoring image, the concentration of said reference points in the region or regions of interest is greater than the concentration of reference points in the rest of the monitoring image.

According to a specific example, the number of reference points used by the monitoring algorithm outside of the region of interest is nil.

By increasing the density of reference points in the regions of interest of the monitoring image, the precision of the monitoring for the visible elements in said regions of interest is maximized. This is achieved at the expense of the precision in the rest of areas of the image—non-critical areas—for which it is not crucial for the precision of the monitoring to be high. Advantageously, the fact that the regions of interest are usually small compared with the entire monitoring image allows the increased density of characteristic points to result in a considerable improvement in precision in monitoring of the critical structures appearing in said regions of interest.

Alternatively, even though more precision than what is provided by conventional monitoring algorithms is not required, the invention would have an additional advantage, which would be to considerably increase the monitoring speed. This is possible because the optimal choice of the characteristic reference points allows reducing their total number, and accordingly, computation time is less.

In a particular embodiment, the control module is configured, for each monitoring image, for:
  determining a numerical model of the clinical scenario comprising the orientation, shape, and position of said clinical scenario from said monitoring image; and
  incorporating the plurality of characteristic reference points determined by the monitoring algorithm belonging to the clinical field in the numerical model associated with said monitoring image.

Throughout this document, the numerical model of a clinical scenario will be understood to be a simplified representation of said clinical scenario using mathematical equations, functions, or formulas expressing ratios, variables, and parameters for studying how said clinical scenario would behave in different situations. This numerical model is capable of reproducing the properties of the physical entity modeled under the limitations imposed by the elements defining said numerical model. For example, a numerical model can computationally represent a biological tissue with geometric elements which determine the structures of said tissue as well as the properties of each of the components of the tissue.

For each monitoring image captured by the viewing unit, the control module determines a numerical model of the captured clinical scenario in order to have available the information associated with said clinical scenario: orientation, shape, and position of the tissues and other elements present in the scenario. Additionally, the numerical models incorporate the characteristic reference points determined by the monitoring algorithm for each monitoring image.

The creation of numerical models in the context of the invention advantageously allows having available all the information that is being analyzed over time to enable determining the necessary transformations between consecutive monitoring images, and thus carrying out the monitoring of the clinical scenario.

In a particular embodiment, the monitoring algorithm is additionally configured for
  determining characteristic reference points in the i-ith monitoring image that are not determined in the immediately preceding monitoring image; and/or
  discarding characteristic reference points in the i-th instant in time that are determined in the monitoring image captured in the immediately preceding instant in time.

As mentioned above, the clinical scenario is not static but rather varies over time due to a number of factors. Thus, the characteristic reference points determined by the monitoring algorithm in a monitoring image may not match the characteristic reference points of the immediately preceding or following monitoring image.

In particular, it is possible for the monitoring algorithm to determine reference points in a monitoring image which had not been determined in the preceding monitoring image; for example, if a high contrast region—which would lead to the determination of a reference point—starts to be visible by the viewing unit in the i-th instant when in instant i−1 it was hidden by another structure or was not part of the field of vision of the viewing unit.

It is also possible that the monitoring algorithm will have to discard reference points determined in a monitoring image in instant i−1 which does not match any of the reference points detected in the i-th monitoring image. Discarding a reference point is to be understood to be that the reference point discarded in instant i-th does not contribute to the determination of i-th transformation.

One reason for discarding is that a characteristic reference point determined in instant i−1, for example from a structure of a specific color, disappears from the field of vision of the viewing unit in the i-th instant in time. It must be noted that in this situation, it is possible for the monitoring algorithm to internally store the reference point detected in instant i−1 on a temporary basis awaiting said point to reappear in the field of vision of the viewing unit in following instants in time.

Another reason why the monitoring algorithm may discard reference points is because they are no longer good candidates on which to base the monitoring of the clinical scenario.

Advantageously, the monitoring algorithm according to a preferred example is adaptable to the changes the clinical scenario itself experiences. This allows analyzing only reference points that can achieve good precision in the monitoring of the clinical scenario such that computational resources are not wasted in the processing of reference points which are not of interest.

In a particular embodiment, the control module is additionally configured for receiving or generating at least one new region of interest in an i-th monitoring image, for i>0, being included in and/or replacing, completely or partially, the set of pre-existing regions of interest.

Throughout the entire clinical event, the control module can receive or generate at least one new region of interest. These new regions of interest will become part of the set of regions of interest according to one of the following options:
the at least one new region of interest can be included in the pre-existing set of regions of interest as an additional region of interest; or
the at least one new region of interest can replace, completely or partially, the pre-existing region or regions of interest; or
the two preceding options can be combined, i.e., one or more of the new regions of interest are included in the set of pre-existing regions of interest as additional regions of interest, and at the same time, another new region or other new regions of interest replace, completely or partially, the pre-existing regions of interest.

Pre-existing regions of interest in a given instant in time are to be understood to be the region or regions of interest which were received or generated by the control module in the preceding instants in time. Likewise, it is understood that a region of interest can be formed by the merging of sub-regions of interest not connected to one another.

Furthermore, a new region of interest:
may differ from a pre-existing region of interest with regard to its position due to the movements the clinical scenario experiences;
may be completely different from any of the pre-existing regions of interest, for example, because in said new region of interest there appear critical structures with respect to which high precision monitoring is to be obtained, and which in preceding instants in time did not appear in the field of vision of the viewing unit.

This embodiment represents a significant advantage since the monitoring of the clinical scenario gradually adapts to the requirements of the clinical event itself. On one hand, it is taken into account that the regions of interest are not static—just as the clinical scenario itself is not static. On the other hand, as the clinical event evolves, the monitoring of the clinical scenario is updated so as to adapt to the appearance/disappearance of critical structures.

In a particular embodiment, the control module and the viewing unit are spatially pre-calibrated such that a match is established between the position of the points in the field of vision of the viewing unit and the position of the points in real space.

Throughout this document, real space will be understood to be the reference space in which the clinical event takes place; for example, if said clinical event is a surgery, real space is the operating table together with the patient, health personnel, and all the devices needed to perform the operation.

In order for the monitoring of the clinical scenario to be precise, it is indispensable for the coordinate system of the system performing said monitoring to have the same references as real space. The pixels or voxels of the field of vision of the viewing unit must therefore match physical points of real space. This match is possible when there is a spatial calibration between the monitoring system itself and real reference space.

In a particular embodiment, the transformation between first and second consecutive monitoring images is a linear transformation corresponding to a rigid solid model of the clinical scenario, wherein the linear transformation verifies that the distance between the characteristic reference points of the first monitoring image transformed by the transformation and the characteristic reference points of the second monitoring image is minimal.

Throughout this document, it will be understood that in a rigid solid model, the bodies are considered to be extensive and undeformable such that the relative positions of the particles constituting said bodies remain constant.

Under this premise, the transformation determined by the monitoring algorithm is a linear type transformation, understanding as such a function defining the relationship between two vectors X' and X through a rotation matrix M and a displacement vector n:

$$X'=M*X+n$$

This linear transformation, known as affine transformation, is such that the distance between two points before and after the transformation is conserved, so it is applicable to those cases in which it is verified that the distance between the characteristic reference points of the first monitoring image transformed by the transformation and the characteristic reference points of the second monitoring image is minimal.

In actuality, a clinical scenario is not a rigid solid since biological tissues undergo deformations with the passage of time, for example, due to the patient's breathing or interaction between the surgical instruments and the patient. However, modeling their behavior as a rigid solid greatly simplifies the clinical scenario monitoring process since linear transformations are computationally much more efficient.

This linear transformation assumes that the clinical scenario is non-deformable over time. Thus, one skilled in the art would not use a transformation of this type to perform monitoring of structures undergoing temporary deformations, such as those characteristic of the clinical scenario of the invention.

Even if one skilled in the art decided to use this type of transformation, he or she would tend to separate the reference points in the monitoring images as much as possible in order to cover, to the extent possible, the entire clinical scenario, and especially to obtain higher precision in the orientation of the referenced elements, thus obtaining a precision in the monitoring of structures that would be insufficient in the context of the invention, particularly in the monitoring of critical structures. To improve this precision, one skilled in the art would use a much larger number of reference points than what any standard monitoring algorithm would determine, which would exponentially increase the computational cost, rendering monitoring of clinical scenarios in quasi real time unviable.

However, the system of the invention is characterized in that the control module receives or generates one or more regions of interest in which the monitoring algorithm determines the highest concentration of characteristic reference points, which surprisingly allows applying a simple linear transformation for carrying out the monitoring of a deformable scenario with high precision in the monitoring of the critical structures visible in the region or regions of interest. On one hand, the regions of interest are of a limited size compared with the size of the monitoring images, and on the other, the concentration of reference points in said regions is greater than in the rest of the monitoring image. Thus, the relative positions between the characteristic reference points of the regions of interest do not undergo or barely undergo variations between consecutive monitoring images.

With this type of transformation, precision in monitoring of the rest of the visible structures in the monitoring images would be lost since the actual deformation that said structures undergo is not taken into account. However, given that these structures are not contained in regions of interest, it can be considered that they are not critical, and therefore their monitoring does not require high precision. The main advantage of applying this model is its simplicity and the low computational cost required by the determination of the transformation.

In a particular embodiment, the transformation is a non-linear transformation corresponding to a deformation model, wherein each pair of characteristic reference points between two consecutive monitoring images has its own match.

Given that the clinical scenario is deformable, using a deformable solid model for modeling it is a more precise and realistic option that that described in the preceding embodiment. Throughout this document, it will be understood that in a deformable solid model, it is considered that the bodies do not meet the condition of a rigid solid, i.e., the deformation they undergo is the result of the change in relative distances between the particles making up the body according to the deformation model subject to the change in position of the reference points used as control points of said deformation model.

In this type of modeling, the transformation determined by the monitoring algorithm is non-linear, with there being a different match between each pair of reference points found in consecutive monitoring images.

This type of transformation is of the type which, a priori, one skilled in the art would use since the clinical scenario deforms over time. However, it would tend to separate the reference points in the monitoring images as much as possible so as to cover, to the extent possible, the entire clinical scenario, and especially achieve smooth deformations, especially in interpolatory deformation models, by making use of a larger area for distributing the reference points. Although the precision obtained in the monitoring of structures would be greater than that obtained by a linear transformation, it would not be focused on the critical structures as is required in the context of the invention. Thus, as there is no information available about the critical structures, one skilled in the art would use a much larger number of reference points than what any standard monitoring algorithm would determine, which would exponentially increase the computational cost, rendering the monitoring of clinical scenarios in quasi real time unviable. It must be observed that the computational cost in this case would even be a much more critical factor than for a linear transformation, since in this case a different match must be determined for each pair of points.

In contrast, using this model in the context of the invention, i.e., using regions of interest with higher concentrations of reference points than in the rest of the monitoring image, entails the advantage of obtaining very high precision in the monitoring of structures belonging to the region or regions of interest. Evidently, the determination of this type of transformation represents a higher computational cost than that corresponding to a single linear transformation for all the reference points.

In a particular embodiment, a transformation for the remaining points which are not characteristic reference points is additionally established by means of an interpolatory deformation model subject to the characteristic reference points having the match given by the transformation.

Additionally, deformable solid modeling allows establishing different transformations for the remaining points of the monitoring images which do not correspond to characteristic reference points. This transformation is estimated by means of interpolation of the transformations determined for the characteristic reference points.

Advantageously, this modeling is even more complete and realistic than the previous modeling, which allows an even greater increase in the precision of the monitoring of the clinical scenario.

In a particular embodiment, the system additionally comprises a spatial positioning and/or orientation unit coupled to the viewing unit, connected to the control module, and controlled by said control module, wherein the control module is additionally configured for moving, displacing, and/or orienting the viewing unit by means of the spatial positioning and/or orientation unit by applying the transformation to the position and orientation before the movement for determining the new position and orientation, so as to capture quasi-static images of the clinical scenario.

The viewing unit can be moved so as to be repositioned and/or reoriented over the course of the clinical event. To that end, the system has an additional unit coupled to the viewing unit: the positioning and/or orientation unit. Throughout this document, it will be understood that the positioning and/or orientation unit comprises mechanical means adapted for displacing and/or orienting the viewing unit. Furthermore, said positioning and/or orientation unit is connected to the control module such that it receives from same instructions for positioning the viewing unit.

Once the transformation has been determined, whether it is linear or non-linear, the viewing unit can be moved (displaced and/or oriented) according to said transformation to carry out the monitoring of the clinical scenario. To that end, the control module applies the transformation to the position and orientation of the viewing unit—before the movement—in order to determine its new position and orientation. The positioning and/or orientation unit receives, from the control module, the new position and orientation of the viewing unit and proceeds to move it according to said new position and orientation (repositioning and/or reorienting it).

After each transformation, the field of vision of the viewing unit will capture quasi-static monitoring images, i.e., it will be perceived that these monitoring images have not varied capture after capture, or that at least said variation was minimal. Thus, the system actively monitors the movement of the clinical scenario such that even though it does experience certain movement, the system will always be positioned with respect to the scenario in the same manner, so the viewing unit—clinical scenario relative position would ideally remain static.

In a particular example, when the transformation according to which the viewing unit is moved (displaced and/or oriented) is of the non-linear type, said transformation corresponds with the most representative transformation of the set of transformations determined for each pair of reference points. In another particular example, said representative transformation also takes into account the remaining transformations of points which are not reference points.

Advantageously, as a result of the repositioning and/or reorientation of the viewing unit, the elements comprised in the clinical scenario are not only perceptible at all times, but also information about the orientation, shape, and position of said elements is available, said information being of great precision for the case of the critical structures contained in the region or regions of interest.

In a particular embodiment, the system additionally comprises a spatial positioning and/or orientation unit coupled to the viewing unit, connected to the control module, and controlled by said control module, wherein the control module is additionally configured for moving, displacing, and/or orienting the viewing unit by means of the spatial positioning and/or orientation unit when the control module automatically detects that the at least one region of interest is located at a smaller distance than a predetermined distance from one of the ends of the field of vision of the viewing unit.

The control module can detect that the region or regions of interest that it has generated or received are located at an end of the field of vision of the viewing unit, in particular when the distance at the end of the field of vision is less than a certain distance or predetermined safety margin. In such case, there is a risk that in the subsequent iterations of the method, the region or regions of interest will disappear from the field of vision.

To avoid this, the control module automatically sends orders to move (reposition and/or reorient) the viewing unit so that the region or regions of interest are located at a greater distance than said predetermined safety margin with respect to the ends of the field of vision of the viewing unit.

This repositioning and/or reorientation of the viewing unit may be an alternative or combined with another or other repositioning and/or reorientation carried out by the spatial positioning and/or orientation unit.

Advantageously, as a result of the repositioning and/or reorientation of the viewing unit, the elements comprised in the clinical scenario are not only perceptible at all times, but also information about the orientation, shape, and position of said elements is available, said information being of great precision for the case of the critical structures contained in the region or regions of interest.

In a particular embodiment, the system additionally comprises a spatial positioning and/or orientation unit coupled to the viewing unit, connected to the control module, and controlled by said control module, wherein the control module is additionally configured for moving, displacing, and/or orienting the viewing unit by means of the spatial positioning and/or orientation unit when the control module receives an order to displace and/or orient the viewing unit through a peripheral and/or other communication paths.

The control module can receive and/or send orders through peripherals. Peripheral is to be understood to be any tool or device acting as an interface between a user or external element and the control module for sending/receiving instructions between each other. Examples of peripherals are joysticks, touch screens, keyboards, or mouses.

Alternatively, the control module can receive and/or send orders through other communication paths, for example, by means of wired communication or wireless communication such as Bluetooth or WiFi.

Thus, the control module can receive instructions, by means of any of the aforementioned communication paths, so as to directly move the viewing unit, repositioning and/or reorienting it by means of the spatial positioning and/or orientation unit.

In a particular example, the medical personnel send orders to the control module for positioning and/or orienting the viewing unit through a peripheral.

This repositioning and/or reorientation of the viewing unit may be an alternative or combined with another or other repositioning and/or reorientation carried out by the spatial positioning and/or orientation unit.

Advantageously, as a result of the repositioning and/or reorientation of the viewing unit, the elements comprised in the clinical scenario are not only perceptible at all times, but also information about the orientation, shape, and position of said elements is available, said information being of great precision for the case of the critical structures contained in the region or regions of interest.

In a particular embodiment, the control module is additionally configured for:
transforming the i-th monitoring image from the transformation such that the distance between the characteristic reference points of the i-th monitoring image and the reference points of the immediately preceding monitoring image is minimal, and
transforming the at least one region of interest from the same transformation in the monitoring image.

In this embodiment, the monitoring images are transformed according to linear or non-linear transformation. Furthermore, so that the region or regions of interest continue to be correctly positioned with respect to the monitoring images, it is necessary to apply the same transformation to said regions of interest.

Therefore, by means of image processing the system will always be positioned with respect to the clinical scenario in the same manner, so the viewing unit—clinical scenario relative position ideally remains static.

Advantageously, information about the orientation, shape, and position of the elements comprised in the clinical scenario is available, said information being of great precision for the case of the critical structures contained in the region or regions of interest.

Another additional advantage of this embodiment is that additional hardware is not required in the system since the presence of a positioning and/or orientation unit is not needed, but rather the control module itself is configured for applying the transformations to the monitoring images.

In a particular embodiment, the control module is additionally configured for transforming the numerical model associated with the i-th monitoring image from the transformation such that the distance between the characteristic reference points of the i-th monitoring image and the reference points of the immediately preceding monitoring image is minimal.

In the event that numerical models have been determined for each monitoring image, when a linear or non-linear transformation is determined, it is necessary for said numerical models to be updated according to the transformation.

Advantageously, by transforming the numerical models, all the information about the clinical scenario—orientation, shape, and position of the elements comprised therein—is available and updated to enable carrying out with precision the monitoring of critical structures.

In a particular embodiment, the monitoring algorithm is a SLAM (Simultaneous Localization and Mapping) type algorithm.

Preferably, the monitoring algorithm is a SLAM type algorithm, initially developed so that a movable robot located in an unknown environment and position is capable of incrementally constructing a map of its environment while at the same time using said map so as to determine its own location. At present, algorithms of this type have also been widely used in other contexts, as is the case of surgical navigation.

In the context of the invention, as already discussed, this algorithm performs two operations: a determination of characteristic reference points and a localization of said points in each i-th instant. Once the position of the reference point cloud has been obtained, the algorithm is capable of inferring, from the displacements of said points, what the relative movement between the clinical scenario and the monitoring system is.

In the invention, a monitoring algorithm based on this known algorithm is preferably used, which advantageously increases the efficiency of the system since the efficacy of said algorithm is highly demonstrated.

In a particular embodiment, the system additionally comprises a critical structure distinction module in communication with the control module, said critical structure distinction module being controlled by the control module, and wherein:

the critical structure distinction module is configured for:
  generating measurements $m_j$ in a plurality of spatial points of its field of vision, where j is an index indicating different instants in time;
  processing the measurements and carrying out a distinction of one or more structures in said plurality of spatial points, and
  sending the information associated with the distinction of structures to the control module;
and wherein the system is additionally characterized in that
  the at least one region of interest received or generated by the control module is selected from a monitoring image depending on the information associated with the j-th distinction of structures, where the j-th instant in time of generating measurements is the closest to the i-th instant in time of capturing the monitoring image.

Throughout this document, critical structure distinction module—or simply distinction module—is to be understood to be a module comprising mechanical, optical, computational, and/or processing means adapted for distinguishing, identifying, or discriminating which tissues or structures of those present in a sample are critical or not critical. In a particular example, the critical structure distinction module discriminates between the tissues on which it is possible to carry out an ablation or cutting operation from those on which it is not.

Firstly, the critical structure distinction module generates a plurality of measurements in different spatial points of its field of vision, understanding as such the space of the clinical scenario on which it has the capacity to perform measurements. Said plurality of measurements are taken at different j-th instants in time, without prejudice to the fact that this notation may vary. Throughout the text, use is made of the index i for identifying instants in time in which an image is acquired by the viewing unit and index j for identifying instants in time in which the acquisition of measurements by the distinction module is carried out. This distinction does not contradict the fact that indices i and j may correspond to the same instants in time in an embodiment of the invention.

Next, the critical structure distinction module processes the measurements and identifies whether or not each of the spatial points on which measurements have been performed correspond to the presence of a structure.

In a preferred embodiment, the type of structure detected is critical, such as a given biological tissue or a specific element of the clinical scenario.

The information obtained by the critical structure distinction module is sent to the control module, for which purpose both modules are connected to one another. The control module uses said information for generating one or more regions of interest in the last monitoring image captured by the viewing unit from pre-established criteria on the measured properties. Alternatively, the control module offers said information to medical personnel for them to select one or more regions of interest in the last monitoring image captured by the viewing unit. Said region or regions of interest must preferably include the structures that the distinction module has identified as critical.

Thus, according to different embodiments of the invention, the region or regions of interest may either be generated by means of the control module directly on a monitoring image or on the critical structure distinction information, or else they can be selected by the medical personnel directly on a monitoring image or on the critical structure distinction information. Preferably, the relationship between the reference systems of the monitoring images and of the critical structure distinction information is known, so the generation or selection of the region or regions of interest in a monitoring image implies that the position of said region or regions of interest with respect to the critical structure distinction information is known—and vice versa.

The selection of the region or regions of interest received by the control module or the generation of the region or regions of interest on the part of the control module are performed based on the information about the coordinates in which the distinction module has identified that the structures are critical. The minimum requirement is that the region of interest must contain at least the region of spatial points encompassing a critical structure according to the information provided by the distinction module. The delimitation is established through a hull, preferably a convex hull. Additionally, the control module can add a certain safety margin that is pre-configured or configurable by the medical personnel to said hull.

The use of a critical structure distinction module allows assuring that monitoring is focused on structures which can actually be considered of interest. This is extremely important in the event that the clinical event is a surgery, as precise and true information about which tissues can be operated on—for example, by means of cutting or ablation—and which must be avoided so as to not inflict unnecessary damage on the patient is available. It is also is extremely important in the event that the clinical event is a treatment, such as, for example, radiological therapy in which it is clinically relevant to limit the application of the radiation used in the treatment to a given region either by increasing its beneficial effect, limiting possible side effects in other tissues, or simply improving the efficiency of the clinical event. Finally, it is likewise important in diagnosis events, especially in those cases in which complex structures requiring detailed visual inspection for a prolonged time without the movements of the clinical scenario preventing it must be displayed.

Thus, the synergistic use of the critical structure distinction and monitoring techniques entails the advantage of maximizing precision of monitoring in the areas of interest to the detriment of precision in non-critical areas which have no clinical relevance.

Alternatively, if more precision than what is provided by conventional monitoring algorithms is not required, the invention would have another additional advantage, which would be to considerably increasing the monitoring speed of the clinical scenario. This is possible because the optimal choice of the characteristic reference points allows reducing their total number, and accordingly, computation time is less.

In a particular embodiment, the critical structure distinction module is spatially pre-calibrated such that a match is established between the position of the points of its field of vision and the position of the points in the field of vision of the viewing unit.

For the monitoring of the critical structures of the clinical scenario to be precise, it is indispensable to know the relationship existing between the coordinate systems of the fields of vision of the viewing unit and of the critical structure distinction module. Therefore, the points in the field of vision of the distinction module in which the latter distinguishes between critical and non-critical structures must match the pixels or voxels of the field of vision of the viewing unit, and therefore, the monitoring images from which the regions of interest are identified. This match is possible when there is a spatial calibration between the critical structure distinction module and the viewing unit.

In a particular embodiment, the critical structure distinction module is spatially pre-calibrated such that a match is established between the position of the points of its field of vision and the position of the points in real space.

For the monitoring of the critical structures of the clinical scenario to be precise, it is indispensable for the coordinate system of the module which distinguishes said critical structures to have the same references as real space. Therefore, the points in the field of vision of the distinction module in which the module distinguishes between critical and non-critical structures must match physical points of real space. This match is possible when there is a spatial calibration between the critical structure distinction module and real reference space.

In a particular embodiment, the system additionally comprises a memory configured for storing, for each spatial point, the measurements carried out by the critical structure distinction module, such that if there are measurements stored in time instant j−1 and new measurements are generated in time instant j, the memory is updated with the measurements of time instant j for each spatial point.

The system additionally comprises a memory in which the measurements performed by the critical structure distinction module for the different spatial points in which said module generates the measurements are saved and updated. This memory must be connected to the critical structure distinction module, which will have read and write permissions in said memory.

Advantageously, based on the content of the memory the most updated measurements at all the points measured by the distinction module will be available to enable establishing in which spatial points a structure can be considered critical or non-critical.

In a particular embodiment, the control module transforms the information about the distinction of structures from the transformation determined by the monitoring algorithm, wherein the j-th instant in time of generating the information about the distinction of structures is the closest to the i-th instant in time of capturing the monitoring image.

For this information about the distinction of structures to be consistent with the monitoring images, and therefore with the region of interest, it is necessary for the control module to transform the information about the distinction of structures from the transformation determined by the monitoring algorithm. Advantageously, all the information handled by the system shares a common reference system once the control module applies the relevant transformations.

In a particular embodiment, the coordinates of the spatial points in which the plurality of measurements of distinction is performed are expressed in the coordinates of the numerical model determined after the transformation.

In preceding embodiments, it is explained that once the monitoring algorithm determines a transformation, the algorithm is used for repositioning/reorienting the physical monitoring system by means of the positioning and/or orientation unit and/or is applied on the monitoring images by means of image processing. Both actions are executed by the control module.

This embodiment is based on the second premise: the transformation determined by the monitoring algorithm has been applied to the monitoring images. In this situation, for the measurements generated by the critical structure distinction module to be carried out on the corrects points of space, it is necessary to inform the distinction module of how the structures have been displaced/rotated in relation to the module or vice versa, i.e., the distinction module will have to generate measurements in the positions of space which would match positions resulting from applying the transformation to real space.

To calculate the position of the spatial points in which the distinction module has to generate the measurements, the corresponding coordinates of the numerical model after applying the transformation on same must be selected. Likewise, the capture of measurements through the distinction module allows enriching the numerical model with this data, taking the value of the measurements to the corresponding site of the numerical model.

In a particular embodiment, the selection of the at least one region of interest is carried out according to a predefined criterion:
  the at least one region of interest comprises at least one nerve, or
  the at least one region of interest comprises at least one tract of brain, or the at least one region of interest comprises at least one blood vessel, or the at least one region of interest is a tissue considered critical, or the at least one region of interest comprises soft tissue, or the at least one region of interest comprises bone, or the at least one region of interest comprises at least one reference marker, or a combination of any of the foregoing.

The region or regions of interest must comprise critical structures, preferably biological tissues. The type of critical tissue depends on the context in which the system is acting, for example, in a surgery it may be of interest to identify nerves or blood vessels on which an ablation or cutting operation must not be performed, or in a tumor resection surgery, the critical tissue must be the actual tumor tissue to be resected.

In a particular example, the region of interest comprises critical structures which are not biological tissues, such as a reference marker. Throughout this document, reference marker is to be understood to be an external fiducial marker which can be fixed to biological tissue (without modifying said tissue), surgical instruments, or any other element present in the clinical scenario.

In a particular embodiment, the field of vision of the critical structure distinction module is limited to:

the at least one region of interest, or the at least one region of interest enlarged by predefined margins.

The time necessary for the critical structure distinction module to be able to identify the critical structures present in its field of vision is not negligible. To optimize tissue distinction speed, the information about the monitoring of critical structures can be used by means of the prioritization of the measurement in critical regions, thus closing a synergy which allows optimizing both techniques for a better application under realistic operating conditions.

That is, to streamline the structure distinction process, said field of vision should be limited so that the critical structure distinction module acts in a more limited region of the space, or to at least give priority to this more limited region of space compared to the rest of the potential field of vision of the critical structure distinction module.

Thus, once at least one region of interest—where said at least one region of interest may or may not originate from the information about the distinction module—has been determined, the field of vision of the distinction module can be limited to said at least one region of interest. Optionally, certain safety margins can be included in order to take into account possible errors in the determination of the at least one region of interest as well as possible movements of the clinical scenario.

With this limitation, the measurement time of the distinction module is reduced and the refresh rate in critical structures is reduced, which represents having information about the position of critical tissues or other critical elements that is updated more often.

In a particular embodiment, the viewing unit comprises:

1) at least one RGB or monochrome camera, or
2) at least one RGB-D or monochrome-D camera with a depth sensor, or
3) at least one camera with spectral, multispectral, or hyperspectral filtering, or
4) ultrasound equipment, or
5) magnetic resonance equipment, or
6) computerized tomography equipment, or
7) preferably polarization-sensitive optical coherence tomography equipment, or
8) a combination of any of the foregoing.

The viewing unit comprises at least one visual element adapted for capturing images of a clinical scenario within its field of vision, said images providing information about the orientation, shape, and position of the clinical scenario.

Any element meeting the preceding premise can be comprised in the viewing unit. Specific examples of viewing unit with these capabilities are those formed by pairs of cameras with stereoscopic capabilities where the combination of two images allows the volumetric reconstruction of objects, the determination of position, and the orientation of surfaces, etc. The captured images do not necessarily have to be two-dimensional, but rather they can be captured, for example, by X-rays or with a CAT scanner, with tissue penetration capacity, and can be represented by means of voxels in three dimensions.

It must be observed that depending on the type of viewing unit, said unit captures more than one initial monitoring image. In such case, the "extra" monitoring image or images provide additional information with respect to what is obtained by means of a single monitoring image, referred to as dominant image, such that the extra information is added to the dominant image.

Preferably, the viewing unit is stereoscopic, i.e., comprises two RGB cameras which capture two initial monitoring images separately.

Both cameras share a field of vision—or at least their fields of vision are very similar—but said field or fields are observed from two different viewpoints. The monitoring algorithm determines a plurality of characteristic reference points in the monitoring images captured by both cameras and establishes a match between the points of both images. By knowing the orientation and relative position between both cameras, depth information (Z axis) from the cameras is triangulated based on the disparity of points between both images. To that end, it is necessary for there to be a good spatial calibration between the cameras. Finally, one of the two images is selected as dominant, and the monitoring algorithm continues to be executed based on the characteristic reference points of said dominant image, but to which points the information about depth obtained as a result of the use of both RGB cameras has been added.

In a particular embodiment, the critical structure distinction module carries out the distinction of one or more tissues by means of one of the following techniques:

laser-induced breakdown spectroscopy (LIBS), or optical coherence tomography (OCT), or polarization-sensitive optical coherence tomography (PS-OCT), or hyperspectral imaging, or linear or non-linear spectrometry based on endogenous or exogenous contrast, or a combination of any of the foregoing.

The critical structure distinction module comprises mechanical, optical, computational, and processing means adapted for distinguishing, identifying, or discriminating which tissues or structures of those present in a sample are critical or non-critical.

Any device or system meeting the preceding premise can act as the critical structure distinction module. Preferably, this distinction module is based on laser-induced breakdown spectroscopy.

In a particular embodiment, the maximum number of monitoring images:
- is a predefined integer greater than or equal to one, or
- is established upon ending the clinical event or session, or
- is established upon reaching a predefined time limit; and/or the maximum number of times the critical structure distinction module generates measurements:
- is a predefined integer greater than or equal to one, or
- is established upon ending the clinical event or session; or
- is established upon reaching a predefined time limit.

Throughout the entire clinical event, the number of times the viewing unit acquires monitoring images, as well as the number of times the distinction module generates measurements so as to obtain information about critical structures can be preset. Likewise, specific actuation times for the viewing unit and/or for the distinction module can be predefined.

Preferably, there is no number of times or time in which the viewing unit and/or the distinction module act, but rather their work ends once the session or clinical event is finished.

In a particular embodiment, the control module is additionally configured for displacing and/or orienting the viewing unit by means of the spatial positioning and/or orientation unit when the control module automatically detects that the at least one region of interest is located at a smaller distance than a predetermined distance from one of the ends of the field of vision of the critical structure distinction module.

The control module can additionally detect that the region or regions of interest that it has generated or received are located at an end of the field of vision of the critical structure distinction module, in particular when the distance to the end is less than a certain predetermined safety distance. In such case, there is a risk that in subsequent iterations of the method, the region or regions of interest will disappear from said field of vision.

To avoid this, the control module automatically sends orders to move the viewing unit—reposition and/or reorient it by means of the spatial positioning and/or orientation unit—so that the region or regions of interest are located at a greater distance than said predetermined safety margin with respect to the ends of the field of vision of the critical structure distinction module.

This repositioning and/or reorientation of the viewing unit may be an alternative or combined with another or other repositioning and/or reorientation carried out by the spatial positioning and/or orientation unit.

Advantageously, as a result of the repositioning and/or reorientation of the viewing unit, the elements comprised in the clinical scenario are not only perceptible at all times, but also information about the orientation, shape, and position of said elements is available, said information being of great precision for the case of the critical structures contained in the region or regions of interest.

All the features described in this specification (including the claims, description, and drawings) can be combined in any combination, with the exception of those combinations of such mutually exclusive features.

DESCRIPTION OF THE DRAWINGS

These and other features and advantages of the invention will become more apparent based on the following detailed description of a preferred embodiment, given solely by way of non-limiting illustrative example in reference to the attached drawings.

DETAILED DISCLOSURE OF THE INVENTION

The present invention describes a system (1) for monitoring a clinical scenario (6). Said clinical scenario (6) is not static, but rather undergoes variations over time for a number of reasons, such as the patient's breathing or the interaction of medical instruments or medical personnel with the tissues of the patient. Due to this movement, there is a need to perform comprehensive monitoring of the elements appearing in the clinical scenario (6), particularly structures of interest; for example, during an ablation surgery it is of interest to know the position, orientation, and shape of certain biological tissues such as nerves or blood vessels.

Figure 1A:
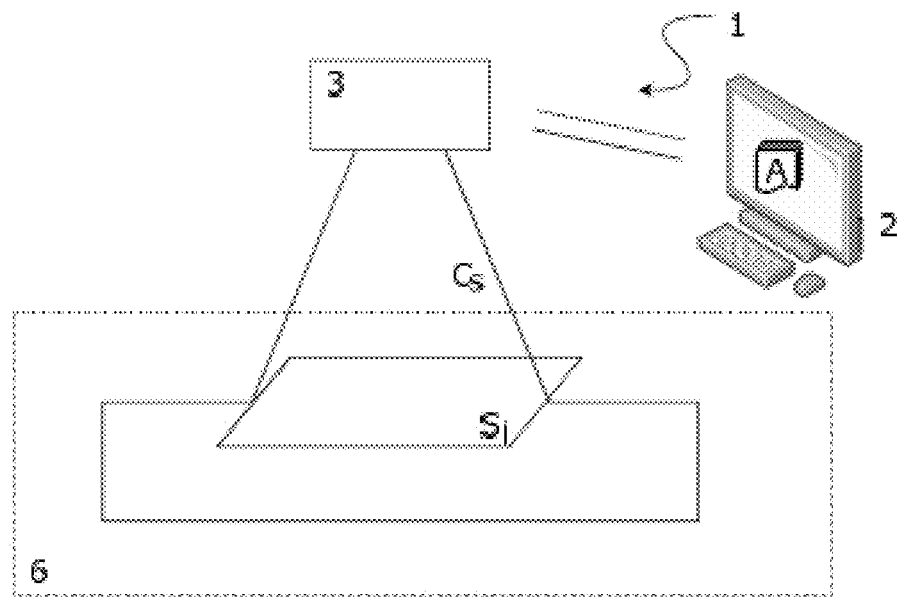
FIGS. 1a and 1b schematically show the state of the art of a system for monitoring a clinical scenario.

FIG. 1a schematically shows a system (1) for monitoring a clinical scenario (6) comprising:
a) a control module (2) with processing capacity and with the capacity to execute the instructions of a monitoring algorithm (A),
b) a viewing unit (3), connected to the control module (2) and controlled by said control module (2), adapted for capturing images of a clinical scenario (6) within its field of vision ($C_s$), wherein the captured images provide information about the orientation, shape, and position of said clinical scenario (6).

A system (1) such as the one described is known in the state of the art, where it is common for both elements to work together. On one hand, the viewing unit (3) is configured for capturing at least one initial monitoring image ($S_0$) and a plurality of monitoring images ($S_i$) of the clinical scenario (6) within its field of vision ($C_s$) in different i-th instants in time. All the monitoring images ($S_0$, $S_i$) are sent by the viewing unit (3) to the control module (2).

In this example shown in FIG. 1a, the clinical scenario (6) comprises the stretcher on which the patient to be operated on is placed, as well as the patient, medical personnel, and the entire environment in which the clinical event occurs. Preferably, the clinical event is a surgery and the clinical scenario is a surgical field comprising, among other elements, the biological tissues of the patient, surgical instruments, or sterile material such as gauzes or swabs.

The control module (2) receives the monitoring images ($S_0$, $S_i$) captured by the viewing unit (3) and carries out on said images a given type of processing. In particular, by means of executing the monitoring algorithm (A), in the initial instant of the clinical event it determines a plurality of initial characteristic reference points ($F_0$) belonging to the clinical scenario (6)—shown in the at least one initial monitoring image ($S_0$)—and establishes their spatial position ($P_0$). As it receives the rest of the monitoring images ($S_i$), it performs the same operation for each of them, i.e., it determines a plurality of characteristic reference points ($F_i$) in each monitoring image ($S_i$) belonging to the clinical scenario (6) and establishes their spatial position ($P_i$).

The characteristic reference points ($F_0$, $F_i$) are pixels or pixel regions of the monitoring images ($S_0$, $S_i$) readily distinguishable with respect to their environment. The distinction criteria of said points are of a varying nature, inter alia:
- characteristic points or regions of the image, such as a mole in the skin or luster in a surgical instrument; or
- specific colors of the image, such as the red color of blood or the metallic of surgical instruments; or
- specific textures of the image, such as the aqueous texture of given fluids; or
- regions of the image with high contrast with respect to their environment, such as the presence of a tumor; or
- regions of the image with high heterogeneity with respect to their environment, such as the presence of a set of blood vessels opposite a homogeneous area such as the skin; or
- a combination of any of the preceding criteria.

In general, the characteristic reference points of two consecutive monitoring images ($S_{i-1}$, $S_i$) match one another, i.e., pairs of points can be established between two consecutive monitoring images. It must be observed that it is possible for certain characteristic reference points to be determined in a single image of the monitoring images, so said points will be lacking said match, at least between two specific instants in time. It must also be noted that for the instant in time i=1, the match between pairs of points is established between the points of the at least one initial monitoring image ($S_0$) and the points of the monitoring image in said instant in time ($S_1$).

As a result of the match between pairs of points, the monitoring algorithm (A) can infer the relative movement between the viewing unit (3) and the clinical scenario (6) over time. Thus, starting from said matches, the monitoring algorithm (A) determines a transformation ($T_i$) relating the position ($P_i$) of the characteristic reference points ($F_i$) determined in instant i with the position ($P_{i-1}$) of the corresponding characteristic reference points ($F_{i-1}$) determined in instant i−1.

Preferably, the monitoring algorithm (A) is a SLAM (Simultaneous Localization and Mapping) type algorithm, the capabilities of which in contexts such as robotics or surgical navigation are highly demonstrated.

Figure 1B:
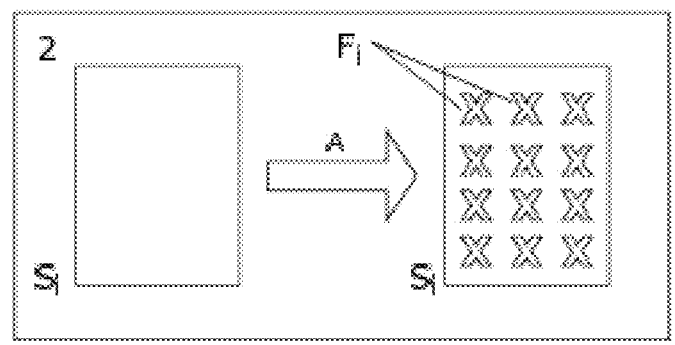

FIG. 1b shows an example of how the monitoring algorithm (A) executed by the control module (2) determines characteristic reference points ($F_i$) in a monitoring image ($S_i$). As can be seen, said points are distributed over the entire monitoring image ($S_i$), covering at least most of the structures of the clinical scenario (6) visible in the monitoring image ($S_i$).

Therefore, no type of specific structure of the clinical scenario (6) is given priority, there being a compromise between the monitoring of all the structures appearing in the monitoring image ($S_i$) —tissues and other elements of the clinical scenario (6) —and the precision attained in said monitoring.

This solution would not be suitable when comprehensive monitoring of certain critical structures is to be performed, or when the number of characteristic reference points ($F_i$) is high, since by means of a characteristic monitoring algorithm (A) of the state of the art, information about the position, orientation, and shape of said structures with insufficient precision and/or a high computational cost would be achieved.

Depending on the context of the clinical event, the critical structures are different; for example, in ablation or cutting surgery comprehensive monitoring of veins and nerves should performed so that medical personnel or a robotic surgical system does not act on said structures. In contrast, in a therapeutic method, the objective of monitoring a critical structure can be to apply the treatment exclusively on that area, such as for example during optical irradiation on cutaneous lesions or the stimulation of nerve tissue. The monitoring of critical structures in diagnosis applications should also be mentioned, where for example it may be of interest to display a critical region such as a node by means of medical imaging techniques for the time needed to complete the diagnosis.

Figure 2A:
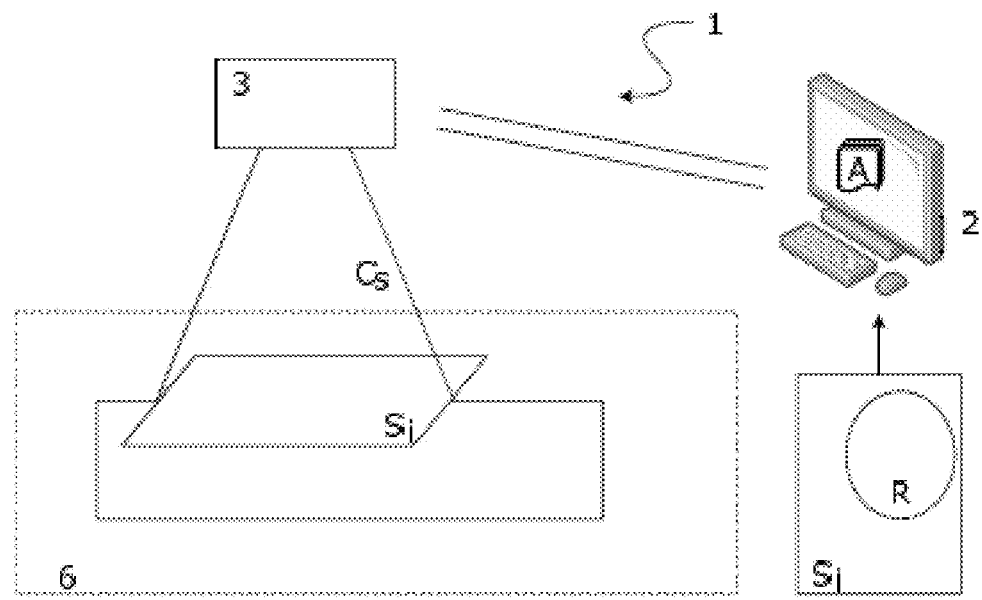
FIGS. 2a and 2b show a diagram of the system for monitoring a clinical scenario according to an embodiment of the invention.
Figure 2B:
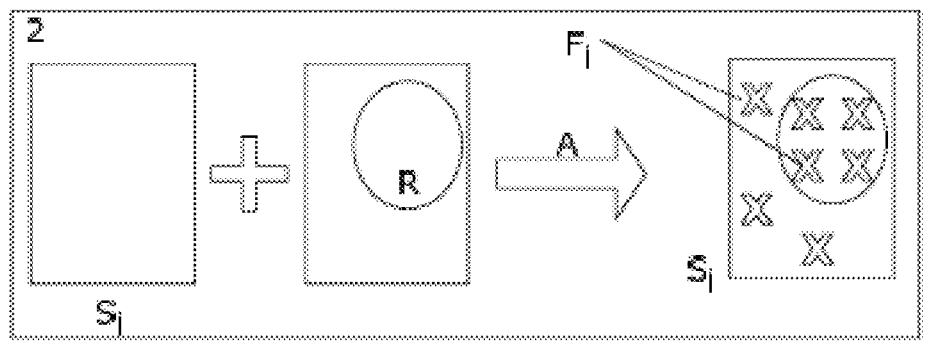

The solution proposed by the invention solves this problem of the state of the art. FIGS. 2a and 2b illustrate the system (1) of the invention, which seeks to improve precision in the monitoring of critical structures of the clinical scenario (6).

This system (1) comprises the same elements as those described in the preceding figures. The viewing unit (3) of the system (1) is preferably a stereoscopic system comprising two RGB cameras. In alternative examples, the viewing unit comprises (3):
- a single RGB camera, or
- at least one monochrome camera, or
- at least one RGB-D or monochrome-D camera with a depth sensor, or
- at least one camera with spectral, multispectral, or hyper-spectral filtering, or
- ultrasound equipment, or
- magnetic resonance equipment, or
- computerized tomography equipment, or
- preferably polarization-sensitive optical coherence tomography equipment, or
- a combination of any of the foregoing.

In the preferred embodiment, it must be observed that since the viewing unit (3) comprises two RGB cameras, two initial monitoring images will be captured separately. The information provided by one of said images, referred to as dominant, is completed with information from the other "extra" monitoring image.

The pixels or voxels of the field of vision ($C_s$) of this viewing unit (3) match physical points of real space in which the clinical event takes place. To that end, preferably, the system (1) for monitoring—control module (2) and viewing unit (3) —is spatially calibrated.

Moreover, the number of monitoring images ($S_i$) acquired by the viewing unit (3) during the clinical event can be a predefined integer greater than or equal to one, be established upon ending said clinical event, or be established upon reaching a predefined time limit.

The system (1) of the invention is characterized in that, unlike the system shown in FIGS. 1a and 1b, the control module (2) is additionally configured for receiving or generating at least one region of interest (R) when the captured monitoring image is the at least one initial monitoring image ($S_0$), and for spatially positioning the at least one region of interest (R) with respect to each monitoring image ($S_i$). Furthermore, the monitoring algorithm (A) is configured such that the concentration of characteristic reference points ($F_i$) in the at least one region of interest (R) is greater than the concentration of characteristic reference points ($F_i$) in the rest of the monitoring image ($S_i$). Preferably, said monitoring algorithm (A) is a modified SLAM algorithm.

In particular, FIG. 2a shows how the control module (2) receives a region of interest (R) and positions it with respect to a monitoring image ($S_i$). This region of interest (R) is a sub-region of the at least one initial monitoring image ($S_0$) in which there appear elements of the clinical scenario (6) with respect to which a higher precision monitoring is to be obtained.

In an alternative embodiment, the control module (2) itself is in charge of generating said region of interest (R). For the sake of simplicity, said FIG. 2a shows only one region of interest (R), but the control module (2) can receive—or generate—more than one region of interest (R).

As already discussed, the region or regions of interest (R) comprise critical structures. Preferably, the critical structures are biological tissues such as nerves, tract of brain, blood vessels, tumors, soft tissue, or bone. Other examples of critical structures other than biological tissues are reference markers present in the clinical scenario (6) or the actual surgical instruments or material.

FIG. 2b shows how the monitoring algorithm (A), taking into account the region of interest (R), determines the plurality of characteristic reference points ($F_i$) in the monitoring image ($S_i$) such that the concentration of said points is higher in the region of interest (R) than in the rest of the monitoring image ($S_i$).

As mentioned above, in general the characteristic reference points ($F_i$) determined for a monitoring image ($S_i$) match the characteristic reference points ($F_{i-1}$) determined for the immediately preceding monitoring image ($S_{i-1}$). However, there are two exceptions which the system (1) of the invention takes into account for reducing the computational cost of processing.

On one hand, it is possible for the monitoring algorithm (A) to identify at least one reference point ($F_i$) in a monitoring image ($S_i$) which was not determined in the preceding monitoring image ($S_{i-1}$). This case may occur, for example, when because of the movement of the clinical scenario (6), elements which previously were not visible and which are susceptible to being identified with a characteristic reference point enter the field of vision ($C_s$) of the viewing unit (3).

Moreover, even though the monitoring algorithm (A) has identified at least one reference point ($F_{i-1}$) in a monitoring image ($S_{i-1}$), said at least one point can be discarded in the immediately following monitoring image ($S_i$). This case may occur either because the structure that has given rise to the at least one reference point is no longer visible in the i-th instant in time (in which case the monitoring algorithm (A) can temporarily store it if it becomes visible again in following instants in time), or simply because the at least one point is no longer a good candidate as a reference point on which to base the monitoring of structures.

This flexibility allows the monitoring algorithm (A) to adapt to the changes the clinical scenario (6) experiences. Thus, it only analyzes the reference points which give rise to good precision in the monitoring of the clinical scenario (6) without wasting computational resources in the processing of points which are not of interest.

In an alternative example, when more precision in the monitoring of critical structures than that provided by conventional monitoring algorithms (A) is not required, with the system (1) of the invention the monitoring speed of structures increases substantially. This is possible as a result of the reduction of the number of characteristic reference points ($F_i$) to be analyzed produced by the optimal choice thereof.

In a preferred example, the region or regions of interest (R) are updated over time. To that end, the control module (2) is additionally configured for receiving or generating at least one new region of interest (R) in a monitoring image ($S_i$), for i>0. A first option is for the new region or regions of interest (R) to be included as part of the already pre-existing set of regions of interest (R), for example, if a new critical structure enters the field of vision ($C_s$) of the viewing unit (3) and detailed monitoring thereof is required. Another option is for the new region or regions of interest (R) to replace one of the pre-existing regions of interest (R), for example, if, due to the movement of the clinical scenario (6) the critical structures of a region of interest (R), have changed in position, shape, and/or orientation. A final option is for a combination of the two preceding options to be produced, i.e., one or more of the new regions of interest (R) are included in the pre-existing set of regions and another new region of interest or other new regions of interest (R) replace one or more pre-existing regions.

Once the characteristic reference points ($F_i$) have been determined and positioned, the monitoring algorithm (A) determines the transformation ($T_i$) relating the position ($P_i$) of the characteristic reference points ($F_i$) determined in instant i with the position ($P_{i-1}$) of the corresponding characteristic reference points ($F_{i-1}$) determined in instant i−1. There are different types of transformation ($T_i$), i.e., linear or non-linear, which entail different degrees of mathematical complexity, and therefore computational cost.

Preferably, the monitoring algorithm (A) determines that the transformation ($T_i$) between two consecutive monitoring images ($S_{i-1}, S_i$) is of the linear type and corresponds to a rigid solid model of the clinical scenario (6). This linear transformation ($T_i$) has to verify that the distance between the characteristic reference points ($F_{i-1}$) of the first monitoring image ($S_{i-1}$) transformed by the transformation ($T_i$) and the characteristic reference points ($F_i$) of the second monitoring image ($S_i$) is minimal.

This linear transformation assumes that the clinical scenario (6) is non-deformable over time. Thus, one skilled in the art would not use a transformation ($T_i$) of this type to perform monitoring of structures undergoing temporary deformations, such as those characteristic of the clinical scenario (6) of the invention.

Even if one skilled in the art decided to use this type of transformation ($T_i$), he or she would tend to separate the reference points ($F_i$) in the monitoring images ($S_i$) as much as possible in order to cover, to the extent possible, the entire clinical scenario (6) because the greater distance between points allows increasing precision in the orientation of the referenced object. Nevertheless, it has been observed that precision in the monitoring of structures is obtained which is insufficient in the context of the invention, particularly in the monitoring of critical structures. To improve this precision, one skilled in the art would use a number of reference points ($F_i$) much greater than what any standard monitoring algorithm (A) would determine, which would exponentially increase the computational cost, rendering the monitoring of clinical scenarios (6) in quasi real time unviable.

However, the system (1) of the invention is characterized in that the control module (2) receives or generates one or more regions of interest (R) in which the monitoring algorithm (A) determines the highest concentration of characteristic reference points ($F_i$), which surprisingly allows applying a simple linear transformation ($T_i$) for carrying out the monitoring of a deformable scenario with high precision in the monitoring of the critical structures visible in the region or regions of interest (R). On one hand, the regions of interest (R) are of a limited size compared with the size of the monitoring images ($S_i$), and on the other, the concentration of reference points ($F_i$) in said regions of interest (R) is greater than in the rest of the monitoring image ($S_i$). Thus, the relative positions between the characteristic reference points ($F_i$) of the regions of interest (R) do not undergo or barely undergo variations between consecutive monitoring images ($S_{i-1}, S_i$). With this type of transformation, precision in the monitoring of the rest of the visible structures in the monitoring images ($S_i$) would be lost since the actual deformation that said structures undergo is not taken into account. However, given that these structures are not contained in regions of interest (R), it can be considered that they are not critical, and therefore their monitoring does not require high precision. The main advantage of applying this model is its simplicity and the low computational cost required by the determination of the transformation ($T_i$).

Alternatively, the monitoring algorithm (A) determines that the transformation ($T_i$) between two consecutive monitoring images ($S_{i-1}, S_i$) is of the non-linear type and corresponds to a deformable solid model of the clinical scenario (6). In this transformation ($T_i$), which is more complex than the aforementioned linear transformation, each pair of reference points ($F_{i-1}, F_i$) between two consecutive monitoring images ($S_{i-1}, S_i$) has its own match, i.e., a different transformation ($T_i$) is applied to each pair of points.

This type of transformation ($T_i$) is of the type which, a priori, one skilled in the art would use since the clinical scenario (6) deforms over time. However, as discussed for the preceding case, he or she would tend to separate the reference points ($F_i$) in the monitoring images ($S_i$) as much as possible so as to cover, to the extent possible, the entire clinical scenario (6) and achieve a smooth and realistic deformation by analyzing the deformation in a larger area. Although the precision obtained in the monitoring of structures would be greater than that obtained by a linear transformation, it would not be focused on the critical structures as is required in the context of the invention. Thus, as there is no information available about the critical structures, one skilled in the art would use a much larger number of reference points ($F_i$) than what any standard monitoring algorithm (A) would determine, which would exponentially increase the computational cost, rendering the monitoring of clinical scenarios (6) in quasi real time unviable. It must be observed that the computational cost in this case would even be a much more critical factor than for a linear transformation, since in this case a different match must be determined for each pair of points.

In contrast, using this model in the context of the invention, i.e., using regions of interest (R) with higher concentrations of reference points ($F_i$) than in the rest of the monitoring image ($S_i$), entails the advantage of obtaining very high precision in the monitoring of structures belonging to the region or regions of interest (R). Evidently, the determination of this type of transformation ($T_i$) represents a higher computational cost than that corresponding to a single linear transformation for all the reference points.

Additionally, non-linear transformation ($T_i$) can be extrapolated to the remaining points of the monitoring image ($S_i$) which are not characteristic reference points ($F_i$) using an interpolatory deformation model. Therefore, even more precision is achieved in the monitoring of structures at the expense of a higher computational cost.

Figure 3:
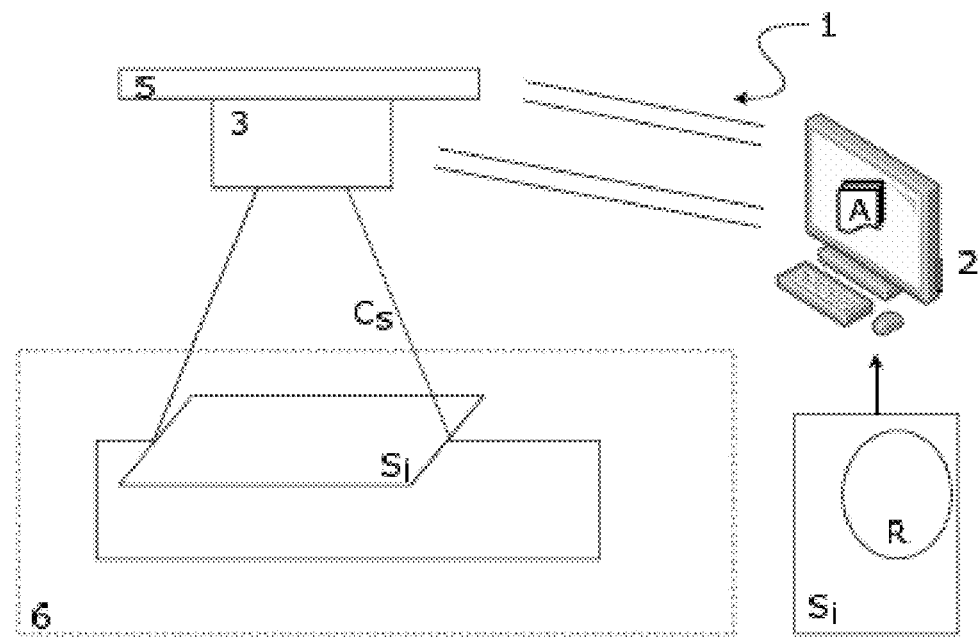
FIG. 3 shows a diagram of the system for monitoring a clinical scenario according to an embodiment of the invention comprising a spatial positioning and/or orientation unit.

FIG. 3 shows an embodiment in which the system (1) additionally comprises a spatial positioning and/or orientation unit (5) coupled to the viewing unit (3). This unit (5) is connected and controlled by the control module (2), which is additionally configured for displacing and/or orienting the viewing unit (3) by means of this spatial positioning and/or orientation unit (5) depending on the transformation ($T_i$) determined by the monitoring algorithm (A).

In an alternative example, the viewing unit (3) is repositioned and/or reoriented if the control module (2) automatically detects that the at least one region of interest (R) is located at a smaller distance than a predetermined distance from one of the ends of the field of vision ($C_s$) of the viewing unit (3). In another alternative example, the viewing unit (3) is repositioned and/or reoriented if the control module (2) receives an order to displace and/or orient the viewing unit (3) through a peripheral—for example, by means of a joystick—and/or through other communication paths—for example, via WiFi.

The objective of this repositioning and/or reorientation of the viewing unit (3) is to achieve capturing quasi-static monitoring images ($S_i$) of the clinical scenario (6), i.e., after repositioning and/or reorienting the viewing unit (3), it will be perceived that the captured monitoring images ($S_i$) have not varied over time, or that at least said variation was minimal. Thus, the system (1) actively monitors the movement of the clinical scenario (6) such that even though it experiences variations, the system (1) is always positioned with respect to the scenario (6) such that the viewing unit (3)—clinical scenario (6) relative position ideally remains static.

In an alternative embodiment, the system (1) does not comprise this spatial positioning and/or orientation unit (5) so the viewing unit (3) remains static. Thus, in order to achieve the same effect of the quasi-static clinical scenario (6), the control module (2) is additionally configured for processing the monitoring images ($S_i$) by applying the transformation ($T_i$) determined by the monitoring algorithm (A) on said images ($S_i$). To that end, the control module (2) transforms the i-th monitoring image from transformation ($T_i$), such that the distance between the characteristic reference points ($F_i$) of this image ($S_i$) and the reference points ($F_{i-1}$) of the immediately preceding monitoring image ($S_{i-1}$) is minimal. Additionally, so that the region or regions of interest (R) continue representing the same area of the monitoring image ($S_i$), the control module (2) also transforms said region or regions (R) from the same transformation ($T_i$).

According to another embodiment, the number of degrees of freedom of the spatial positioning and/or orientation unit (5) is limited, for example, to two movements on a horizontal plane, and therefore compensation for the movements is not sufficient. This embodiment combines the use of this spatial positioning and/or orientation unit (5) and the application of the transformation ($T_i$) determined by the monitoring algorithm (A) on the images ($S_i$) after the compensation applied by the spatial positioning and/or orientation unit (5), improving the end result since this latter transformation gives rise to minor displacements and rotations.

In a particular example, the system (1) of FIGS. 2a, 2b, and 3 is configured, for each monitoring image ($S_i$), for determining a numerical model of the clinical scenario (6) comprising the orientation, shape, and position of said clinical scenario (6) from said monitoring image ($S_i$). Additionally, the system (1) is configured for incorporating the plurality of characteristic reference points ($F_i$) determined by the monitoring algorithm (A) belonging to the clinical field in the numerical model associated with said monitoring image ($S_i$). A data structure intended for storing this numerical model comprises the monitoring image ($S_i$) as well as data sub-structures intended for storing other elements, such as for example, surface and volume model equations, reference points, or other images representing scalar values of properties.

Additionally, in order to achieve the aforementioned effect of a quasi-static clinical scenario (6), the control module (2) is additionally configured for transforming the numerical model associated with the monitoring image ($S_i$) from transformation ($T_i$) such that the distance between the characteristic reference points ($F_i$) of the monitoring image ($S_i$) and the reference points ($F_{i-1}$) of the immediately preceding monitoring image ($S_{i-1}$) is minimal.

Figure 4:
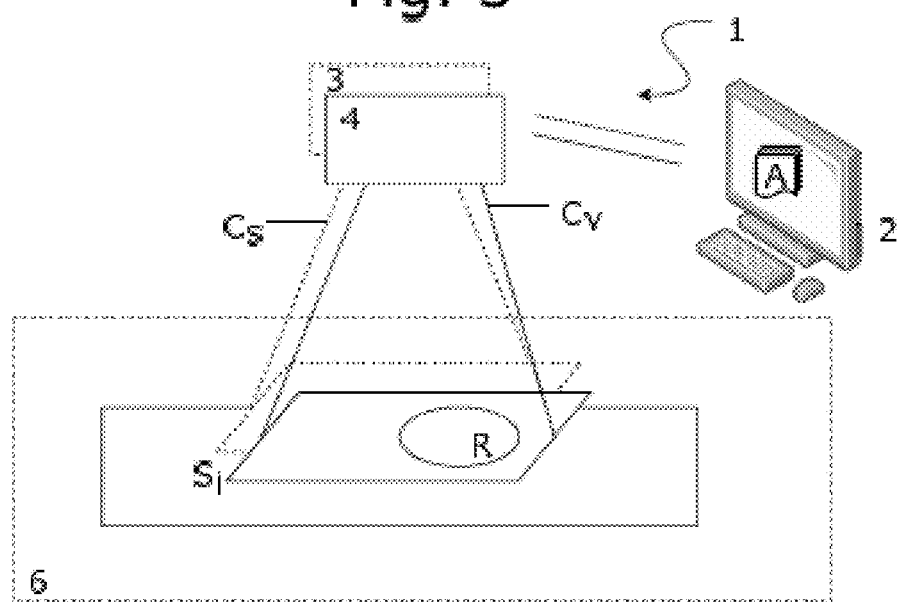
FIG. 4 shows a diagram of the system for monitoring a clinical scenario according to an embodiment of the invention comprising a critical structure distinction module.

FIG. 4 shows an embodiment in which the system (1) additionally comprises a critical structure distinction module (4). Said module has the function of distinguishing, identifying, or discriminating which tissues or structures of those present in the clinical scenario (6) are critical or non-critical. For example, in the context of ablation or cutting surgery, the critical structure distinction module discriminates between the tissues on which it is possible to carry out an ablation or cutting operation from those in which it is not. In the context of a clinical event of treatment, the distinction module discriminates between the tissues on which the treatment must be applied from those on which it must not. And finally, in the case of a diagnosis operation, the diagnosis module discriminates between the tissues of interest on which the diagnosis is to be focused from those which are irrelevant for determining the healthy or pathological condition of the patient.

Preferably, the technique used by the critical structure distinction module (4) is laser-induced breakdown spectroscopy (LIBS). In other alternative examples, the technique is one of the following:
- optical coherence tomography (OCT), or
- polarization-sensitive optical coherence tomography (PS-OCT), or
- hyperspectral imaging, or
- linear or non-linear spectrometry based on endogenous or exogenous contrast, or
- a combination of any of the preceding techniques.

This additional module, which communicates with the control module (2) and is controlled by said control module (2), generates measurements ($m_j$) in a plurality of spatial points of its field of vision ($C_v$), where j is an index indicating different instants in time. In a particular example, the measurements ($m_j$) carried out by the critical structure distinction module (4) is stored in a memory comprised in the system (1). These measurements ($m_j$) must furthermore be updated in subsequent time instants.

The number of measurements ($m_j$) generated by the critical structure distinction module (4) during the clinical event may be is a predefined integer greater than or equal to one, may be established upon ending said clinical event, or may be established upon reaching a predefined time limit.

Once the measurements ($m_j$) have been taken, the critical structure distinction module (4) processes them and carries out a distinction of one or more structures ($D_j$) in said plurality of spatial points ($m_j$). Finally, it sends the information associated with the distinction of structures ($D_j$) to the control module (2). In a preferred embodiment, for this information and the monitoring of structures to be consistent, the control module (2) transforms the information about the distinction of structures ($D_j$) from the transformation ($T_i$) determined by the monitoring algorithm (A).

This information associated with the distinction of structures ($D_j$) serves as a basis for selecting the at least one region of interest (R) of a monitoring image ($S_0$, $S_i$) taking into account that the instant of generating measurements ($m_j$) must be the closest to the instant in time of capturing the monitoring image to minimize the effects of movement of the clinical scenario (6).

In a particular example, the control module (2) generates the at least one region of interest (R) from the information associated with the distinction of structures ($D_j$). The minimum requirement is that the region of interest (R) must contain at least the region of spatial points encompassing a critical structure according to the information provided by the distinction module (4). Preferably, the delimitation is established through a hull. More preferably, the hull is convex. Additionally, the control module (2) adds a certain safety margin to said hull by generating a hull expanded a determined distance.

In another particular example, the medical personnel selects the at least one region of interest (R) from the information associated with the distinction of structures ($D_j$) and sends it to the control module (2).

As can be seen in FIG. 4, the fields of vision ($C_s$, $C_v$) of the viewing unit (3) and of the critical structure distinction module (4) do not have to encompass the same extension. Preferably, both fields of vision at least partially overlap one another.

For the monitoring of the critical structures of the clinical scenario (6) to be precise, both fields of vision ($C_s$, $C_v$) are required to have the same coordinate system. Thus, the critical structure distinction module (4) and the viewing unit (3) of the system (1) shown in FIG. 4 are spatially calibrated. Additionally, the critical structure distinction module (4) is also spatially calibrated so that its system has the same references as the real space in which the clinical event takes place.

In a preferred embodiment, the field of vision of the critical structure distinction module (4) is limited to the region of interest (R) with or without predefined safety margins. Therefore, measurement time of the distinction module (4) is reduced and the refresh rate in critical structures is increased.

In an alternative embodiment, the system (1) of FIG. 4 additionally comprises a spatial positioning and/or orientation unit (5) coupled to the viewing unit (3). This unit (5) is connected and controlled by the control module (2), which is additionally configured for displacing and/or orienting the viewing unit (3) by means of this spatial positioning and/or orientation unit (5) if the control module (2) automatically detects that the at least one region of interest (R) is located at a smaller distance than a predetermined distance from one of the ends of the field of vision ($C_v$) of the critical structure distinction module (4).

The invention claimed is:

1. A system for monitoring biological tissues or other elements or structures that are present in a clinical scenario, the clinical scenario being a set of elements or structures on which a surgery, a diagnosis event, or a treatment event takes place, the system comprising:
   a) a control module with a processing capacity; and
   b) a viewing unit connected to the control module and controlled by the control module, the viewing unit configured to capture images of a clinical scenario within a field of vision ($C_s$), wherein captured images provide information about an orientation, shape, and position of the clinical scenario;

wherein the control module and the viewing unit are configured to:
   capture at least one initial monitoring image ($S_0$) of the clinical scenario within the field of vision ($C_s$) of the viewing unit;
   capture a plurality of monitoring images ($S_i$) of the clinical scenario within the field of vision ($C_s$) of the viewing unit in different instants in time, where i is an index indicating a time instant of capture of a captured i-th monitoring image ($S_i$);
   executing a monitoring algorithm (A) of the control module to:
      determine a plurality of initial characteristic reference points ($F_0$) belonging to the clinical scenario and shown in at least one initial monitoring image ($S_0$) to establish a spatial position ($P_0$);

determine a plurality of characteristic reference points ($F_i$) for each of monitoring images ($S_i$), a plurality of characteristic reference points ($F_i$) belonging to the clinical scenario, which match characteristic reference points determined in an immediately preceding monitoring image ($S_{i-1}$), and establishing their spatial position ($P_i$);

determine a transformation ($T_i$) relating a position ($P_i$) of the characteristic reference points ($F_i$) determined in index i with a position ($P_{i-1}$) of corresponding characteristic reference points ($F_{i-1}$) determined in instant i–1;

wherein the control module is further configured to:

receive or generate at least one region of interest (R) when the captured monitoring image is the at least one initial monitoring image ($S_0$), and spatially position the at least one region of interest (R) with respect to each monitoring image ($S_i$), wherein the monitoring algorithm (A) is configured such that a concentration of characteristic reference points ($F_i$) in the at least one region of interest (R) is greater than a concentration of characteristic reference points ($F_i$) in a remainder of the monitoring image ($S_i$); and wherein the system further comprises at least one of a spatial positioning or orientation unit coupled to the viewing unit, the at least one of the spatial position or orientation unit connected to the control module, and controlled by the control module, the control module further configured to perform at least one of moving, displacing, or orienting the viewing unit using at least one of the spatial positioning or orientation unit by applying the transformation ($T_i$) to a position and orientation before the movement for determining a new position and orientation, so as to capture quasi-static images of the clinical scenario.

2. The system according to claim 1, wherein for each monitoring image ($S_i$) the control module is further configured, to determine a numerical model of the clinical scenario comprising the orientation, shape, and position of the clinical scenario from the monitoring image ($S_i$), and incorporate the plurality of characteristic reference points ($F_i$) determined by the monitoring algorithm (A) belonging to the clinical field in the numerical model associated with the monitoring image ($S_i$).

3. The system according to claim 2, wherein the control module is additionally configured for transforming the numerical model associated with the i-th monitoring image ($S_i$) from the transformation ($T_i$) such that the distance between the characteristic reference points ($F_i$) of the i-th monitoring image ($S_i$) and the reference points ($F_{i-1}$) of the immediately preceding monitoring image ($S_{i-1}$) is minimal.

4. The system according to claim 1, wherein the monitoring algorithm (A) is additionally configured to at least one of: determine characteristic reference points ($F_i$) in the i-th monitoring image ($S_i$) that are not determined in the immediately preceding monitoring image ($S_{i-1}$); or discard characteristic reference points ($F_{i-1}$) in the i-th index in time that are determined in the monitoring image ($S_{i-1}$) captured in the immediately preceding instant in time.

5. The system according to claim 4, wherein the control module is configured to:

transform the i-th monitoring image ($S_i$) from transformation ($T_i$) such that a distance between the characteristic reference points ($F_i$) of the i-th monitoring image ($S_i$) and the reference points ($F_{i-1}$) of the immediately preceding monitoring image ($S_{i-1}$) is minimal, and transform the at least one region of interest (R) from the same transformation ($T_i$) in the monitoring image ($S_i$).

6. The system according to claim 1, wherein the control module is further configured to receive or generate at least one new region of interest (R) in an i-th monitoring image ($S_i$), where i>0, the new region of interest (R) being at least one of included in and replacing, completely or partially, the set of pre-existing regions of interest.

7. The system according to claim 1, wherein the control module and the viewing unit are spatially pre-calibrated such that a match is established between the position of the points in the field of vision ($C_s$) of the viewing unit and a position of the points in real space.

8. The system according to claim 1, wherein the transformation ($T_i$) between first and second consecutive monitoring images ($S_{i-1}$, $S_i$) is a linear transformation corresponding to a rigid solid model of the clinical scenario, wherein the linear transformation verifies that a distance between the characteristic reference points ($F_{i-1}$) of the first monitoring image ($S_{i-1}$) transformed by the transformation ($T_i$) and the characteristic reference points ($F_i$) of the second monitoring image ($S_i$) is minimal.

9. The system according to claim 1, wherein the transformation ($T_i$) is a non-linear transformation corresponding to a deformation model, wherein each pair of characteristic reference points ($F_{i-1}$, $F_i$) between two consecutive monitoring images ($S_{i-1}$, $S_i$) has its own match.

10. The system according to claim 9, wherein a transformation for the remaining points which are not characteristic reference points ($F_i$) is additionally established by an interpolatory deformation model subject to the characteristic reference points ($F_i$) having the match given by the transformation ($T_i$).

11. The system according to claim 1, wherein the control module is further configured to perform at least one of moving, displacing, or orienting the viewing unit using at least one of the spatial positioning or orientation unit when the control module automatically detects that the at least one region of interest (R) is located at a smaller distance than a predetermined distance from one of the ends of the field of vision ($C_s$) of the viewing unit.

12. The system according to claim 1, wherein the control module is further configured to perform at least one of moving, displacing, or orienting the viewing unit using at least one of the spatial positioning or orientation unit when the control module receives an order to at least one of displace or orient the viewing unit through at least one of a peripheral or other communication paths.

13. The system according to claim 1, wherein the monitoring algorithm (A) is a Simultaneous Localization and Mapping (SLAM) type algorithm.

14. The system according to claim 1, wherein the system further comprises a critical structure distinction module in communication with the control module, the critical structure distinction module being controlled by the control module, and wherein:

the critical structure distinction module is configured to:

generate measurements ($m_j$) in a plurality of spatial points of its field of vision ($C_v$), where j is an index indicating different instants in time;

process the measurements ($m_j$) and carry out a distinction of one or more structures ($D_j$) in said plurality of spatial points, and send the information associated with a distinction of structures ($D_j$) to the control module (2);

and wherein the at least one region of interest (R) received or generated by the control module is selected from a monitoring image ($S_0$, $S_i$) depending on information associated with a j-th distinction of structures ($D_j$), where a j-th instant in time of generating measurements ($m_j$) is closest to the i-th instant in time of capturing the monitoring image ($S_0$, $S_i$).

15. The system according to claim 14, wherein the critical structure distinction module is spatially pre-calibrated such that a match is established between a position of the points of its field of vision ($C_v$) and a position of the points in the field of vision ($C_s$) of the viewing unit (3).

16. The system according to claim 14, wherein the critical structure distinction module is spatially pre-calibrated such that a match is established between the position of the points of its field of vision ($C_v$) and the position of the points in real space.

17. The system according to claim 14, wherein the system further comprises a memory configured for storing, for each spatial point, the measurements ($m_j$) carried out by the critical structure distinction module, such that if there are measurements stored in time instant j−1 ($m_{j-1}$) and new measurements are generated in time instant j ($m_j$), the memory is updated with the measurements of time instant j for each spatial point.

18. The system according to claim 17, wherein the control module transforms the information about the distinction of structures ($D_j$) from transformation ($T_i$) determined by the monitoring algorithm (A), wherein the j-th instant in time of generating the information about the distinction of structures ($D_j$) is the closest to the i-th instant in time of capturing the monitoring image ($S_0$, $S_i$).

19. The system according to claim 14, wherein coordinates of the spatial points in which the plurality of measurements ($m_j$) of distinction is performed are expressed in the coordinates of the numerical model determined after transformation ($T_i$).

20. The system according to claim 1, wherein a selection of the at least one region of interest (R) is carried out according to a predefined criterion, wherein the at least one region of interest (R) comprises at least one of a nerve, tract of brain, blood vessel, a tissue considered critical, soft tissue, bone, or at least one reference marker.

21. The system according to claim 20, wherein the field of vision ($C_v$) of the critical structure distinction module includes:

the at least one region of interest (R), or the at least one region of interest (R) enlarged by predefined margins.

22. The system according to claim 21, wherein the control module is further configured to at least one of displace or orient the viewing unit by means of at least one of the spatial positioning or orientation unit when the control module automatically detects that the at least one region of interest (R) is located at a smaller distance than a predetermined distance from one of the ends of the field of vision ($C_v$) of the critical structure distinction module.

23. The system according to claim 1, wherein the viewing unit comprises at least one of a RGB or monochrome camera, a RGB-D or monochrome-D camera with a depth sensor, a camera with spectral, multispectral, or hyperspectral filtering, ultrasound equipment, magnetic resonance equipment, computerized tomography equipment, and polarization-sensitive optical coherence tomography equipment.

24. The system according to claim 23, wherein the critical structure distinction module carries out the distinction of one or more structures ($D_j$) utilizing at least one of laser-induced breakdown spectroscopy (LIBS), optical coherence tomography (OCT), polarization-sensitive optical coherence tomography (PS-OCT), hyperspectral imaging, linear spectrometry based on endogenous or exogenous contrast, or non-linear spectrometry based on endogenous or exogenous contrast.

25. The system according to claim 1, wherein:

a maximum number of monitoring images ($S_i$) is at least one of: a predefined integer greater than or equal to one, established upon ending a clinical event or session, and established upon reaching a predefined time limit, and a maximum number of times the critical structure distinction module generates measurements ($m_j$) is at least one of: a predefined integer greater than or equal to one, established upon ending the clinical event or session, and established upon reaching a predefined time limit.

* * * * *